(12) United States Patent
DeHarde et al.

(10) Patent No.: US 6,716,199 B2
(45) Date of Patent: Apr. 6, 2004

(54) SAFETY SYRINGE SYSTEM

(76) Inventors: Lawrence G. DeHarde, 2916 Dautrieve Dr., Chalmette, LA (US) 70043; Michael H. Deharde, 3108 Delambert, Chalmette, LA (US) 70043

( * ) Notice: Subject to any disclaimer, the term of this patent is extended or adjusted under 35 U.S.C. 154(b) by 0 days.

(21) Appl. No.: 09/908,401

(22) Filed: Jul. 18, 2001

(65) Prior Publication Data

US 2003/0028171 A1 Feb. 6, 2003

(51) Int. Cl.[7] .............................. A61M 5/00; A61M 5/32
(52) U.S. Cl. ...................... 604/263; 604/192; 604/110
(58) Field of Search .............................. 604/198, 192, 604/110, 263, 187, 113, 195, 197

(56) References Cited

U.S. PATENT DOCUMENTS 5,037,402 A * 8/1991 Bartman .................... 604/198
5,312,372 A * 5/1994 DeHarde et al. ............ 604/198
5,411,492 A * 5/1995 Sturman et al. ............ 604/263

* cited by examiner

Primary Examiner—LoAn H. Thanh
Assistant Examiner—Matthew F DeSanto
(74) Attorney, Agent, or Firm—Joseph T. Regard, Ltd PLC

(57) ABSTRACT

A system for converting an off-the-shelf syringe into a safety syringe for preventing accidental needle stick or infection. The preferred embodiment of the present invention is configured to mount to an off-the-shelf syringe via threaded, snap, permanent, or other engagement to the cannula hub of the syringe, wherein the device may include the needle for mounting to the syringe, or via barrel rings configured to mount about the barrel of the syringe. The device is configured to convert the syringe into a safety syringe including a protective cover in longitudinal communication with the syringe needle, the protective cover configured to longitudinally envelope the base of the needle in a storage position, and engage and cap the needle tip in a protected configuration after the instrument has been utilized.

6 Claims, 9 Drawing Sheets

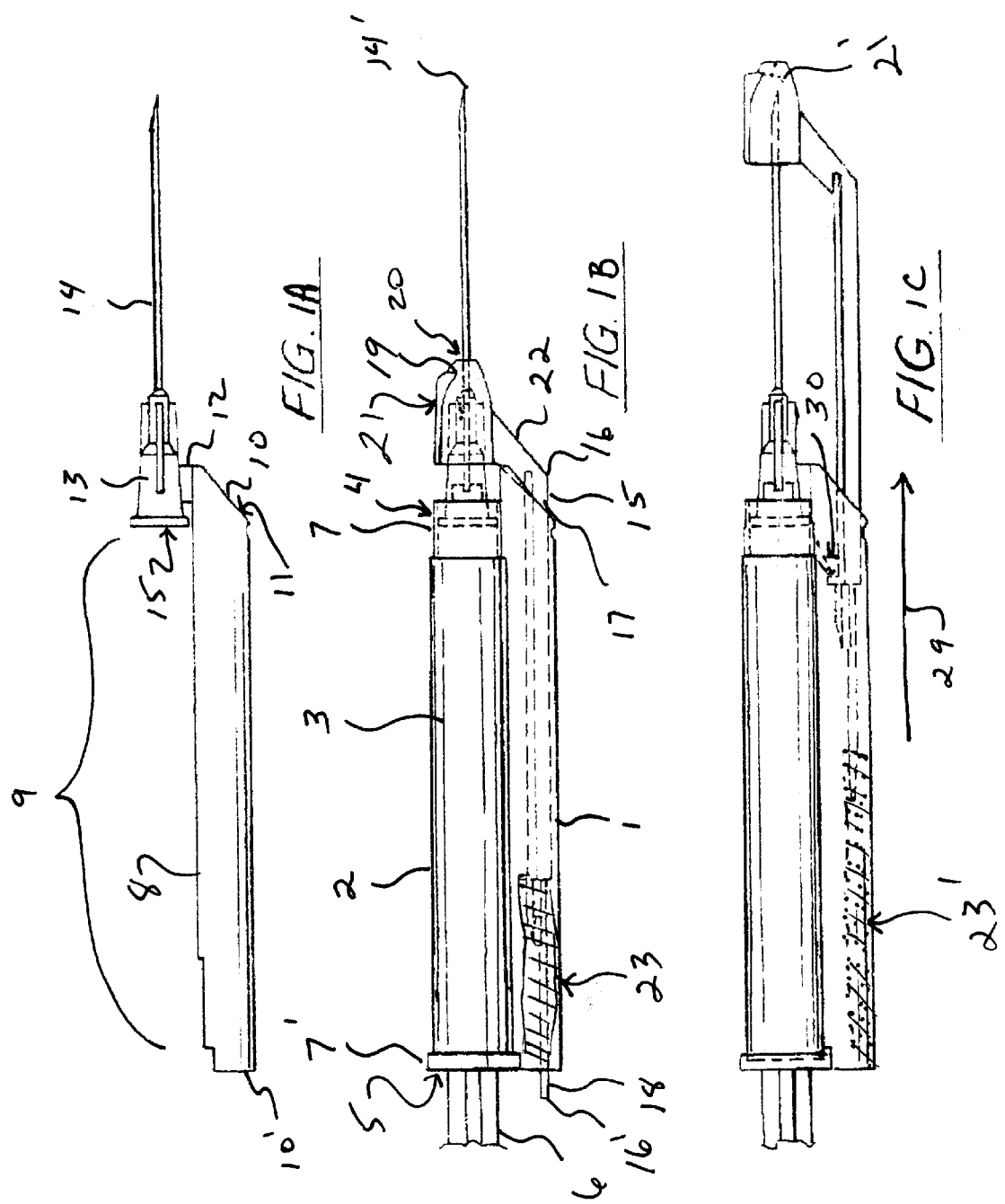

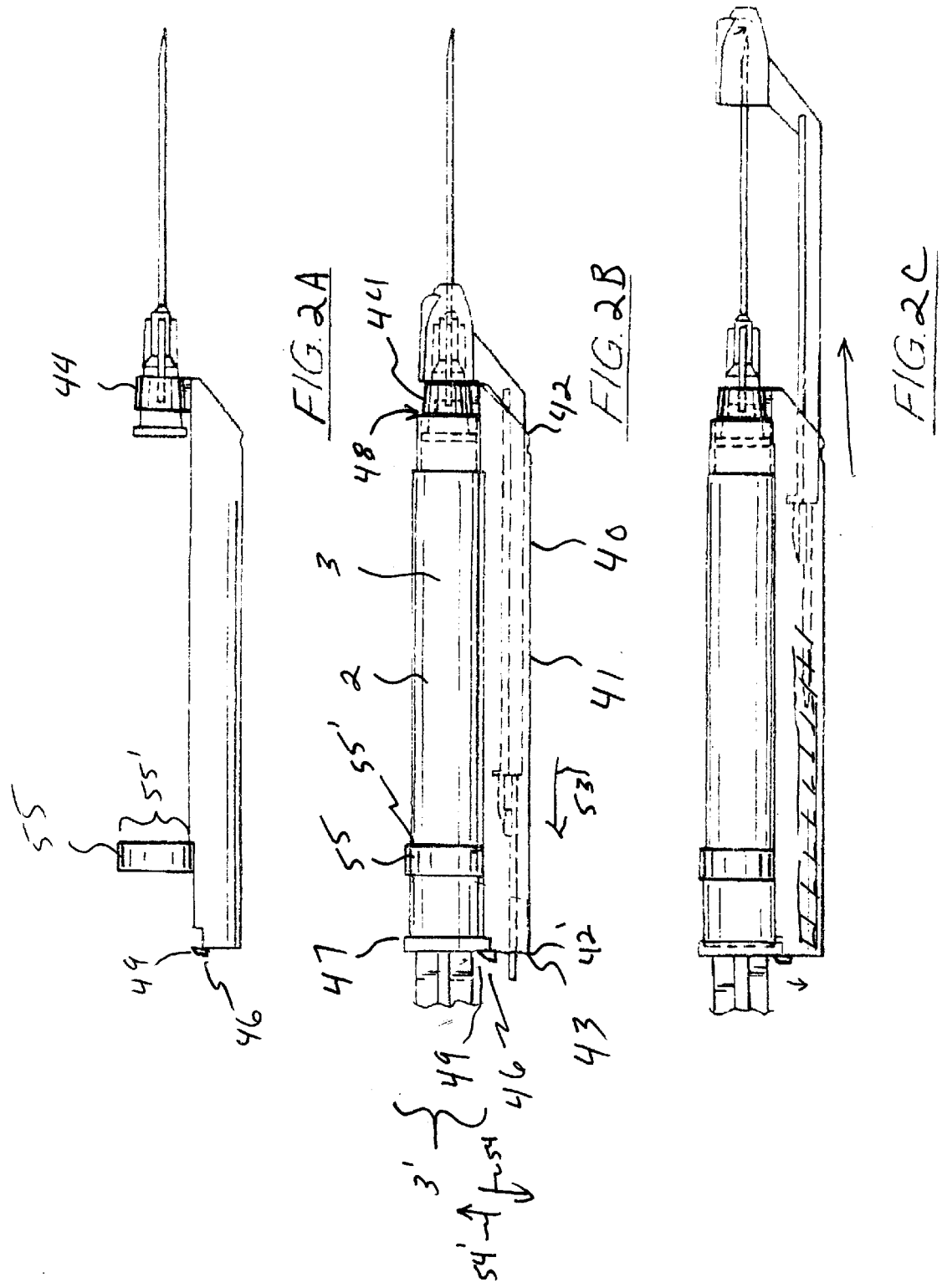

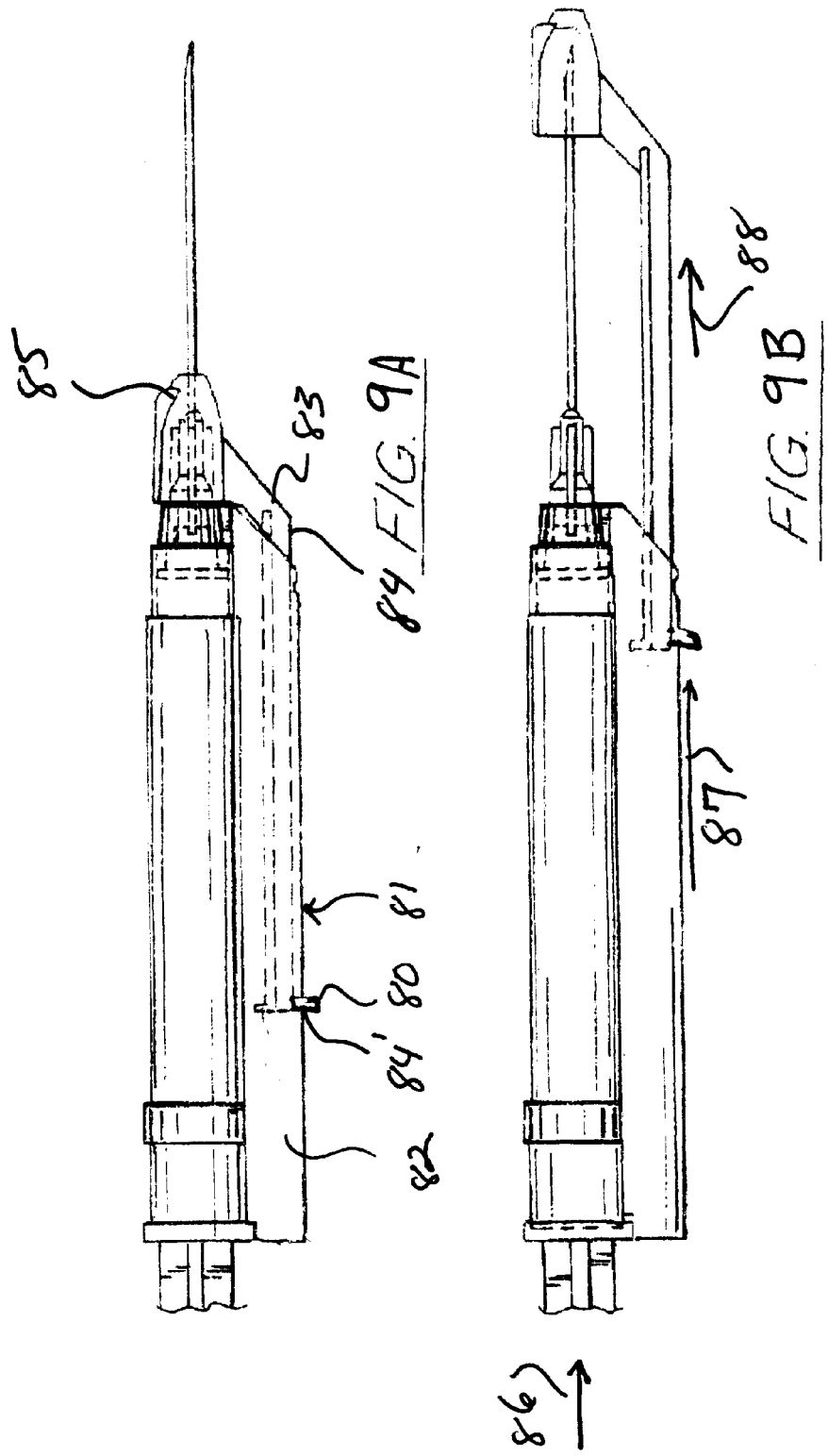

SAFETY SYRINGE SYSTEM

TECHNICAL FIELD OF THE INVENTION

The present invention relates to systems for preventing infection from unsterile hypodermic needles or the like, and more particularly to a system for preventing needle stick or re-use of unsterile hypodermic needles or like items.

The preferred embodiment of the present invention teaches a system for converting an off-the-shelf syringe into a safety syringe for preventing accidental needle stick or infection. The preferred embodiment is configured to mount to an off-the-shelf syringe via threaded, snap on, adhesive, permanent, or other engagement to the collar of the syringe, wherein the device may include the needle with a hub for mounting to the syringe, or in an alternative embodiment, via barrel rings configured to mount about the barrel of the syringe.

The device is configured to convert the syringe into a safety syringe including a protective cover in longitudinal communication with the syringe needle, the protective cover configured to longitudinally envelope the base of the needle in a storage position, and engage and cap the needle tip in a protected configuration after the instrument has been utilized.

A housing is provided for enclosing a shaft longitudinally aligned with the barrel of the syringe so that its first end is in general communication with the protective cover, and its second end is configured to engage an activation button generally situated in the vicinity of the end of the syringe distal the needle, the housing further including a spring or the like for providing bias to urge the protective cap, via the shaft, from the base of the needle to cover the needle tip.

An alternative embodiment of the present invention teaches a one-piece, monolithic syringe body including the housing, while another alternative teaches a system without a spring bias, requiring manual manipulation of the shaft to urge the cap to the protective position.

BACKGROUND OF THE INVENTION

Since the early 1980's it has been recognized that instruments which come into contact with human tissue fluids can comprise biohazard, particularly when those instruments come into contact with HIV, hepatitis, and other tissue infected with contagion.

Further, it has been recognized that the sharing and re-usage of disposable needles has transmitted HIV among intravenous drug users.

Consequently, there has evolved a plethora of re-designs of existing hypodermic syringes and related devices, wherein there has been incorporated features to prevent infection and, in the case of disposable systems, reuse.

Often, the distraction surrounding a medical emergency or like situation may result in used syringes not being identified as being particularly contaminated. This could result in the re-use of the syringe by a medical professional and potential contamination resulting therefrom.

Additionally, if the syringe is not properly disposed of an addict may thereafter utilize it to administer illegal drugs to himself and others, spreading the virus, bacteria, disease, or anything else which may be present on the point and shaft of the hollow metal needle.

It is for this reason that an easily operated, consistent and tamper proof, syringe needle capping system is needed, so that the utilized needle may be automatically capped immediately after use, even in the heat of a medical emergency, without distraction and in a consistent and unfailing manner.

Patents of relevance include:

U.S. Pat. No. 4,702,738 attempts to address the problem of inadvertent pricks, but lacks a solid locking means as the system would appear to be locked solely by spring force, which could be overcome.

U.S. Pat. No. 4,725,267 addresses the problem of inadvertent pricks by covering the point of the needle, but activating it requires the operator to work in the area of the point of the needle, increasing the potential contamination risk simply to cover the needle. Further, the cover could be forced back exposing the needle, potentially causing a prick.

U.S. Pat. No. 4,790,828, issued in 1988, teaches a "Self-capping Needle Assembly", wherein in FIGS. 1, 2 and 6, there is contemplated a locking needle capping assembly utilizing biased blockage means, albeit distinguishable in operation and design from that contemplated by the present invention.

Namely, the activation system which must be manually lifted in the '828 system is more cumbersome to operate with one hand and could actually encourage needle stick.

U.S. Pat. No. 4,804,371 attempts to address the problem of inadvertent pricks by covering the needle, but can be pushed out of the way if one desires to overcome the system, thereby preventing re-use.

U.S. Pat. No. 4,994,046, issued in 1991, discloses a "Needle Guard for Syringe", wherein there is taught a side mounted apparatus for controlling the shield means, albeit completely distinguishable in form and operation from the present invention.

U.S. Pat. No. 4,863,434, issued in 1989 describes an "automatic needle sheath for disposable syringe" wherein a needle capping assembly is disclosed (note FIG. "A") offering biased blocking members to cover the needle. However, the '434 patent fails to contemplate an efficient, inexpensive, and safe system as taught in the present invention.

U.S. Pat. No. 4,936,830 addresses the problem of inadvertent pricks and reuse, but works only on pre-filled syringes.

U.S. Pat. No. 4,986,818, issued Jan. 22, 1991, and U.S. Pat. No. 4,990,141, issued Feb. 5, 1991, also teaches single use syringes utilizing a type of safety capping assembly again distinguishable from the present invention, but nonetheless pertinent with respect to the generalized concept of a single use syringe system.

U.S. Pat. No. 5,026,353 issued Jun. 25, 1991 teaches a "multi-chamber safety syringe", contemplating a rather bulky, complicated, and expensive system for preventing needle stick, wherein there is taught essentially the incorporation of dual spring biased reciprocating pistons on opposing sides of the syringe to force forward a capping assembly.

As taught, the device of the '353 patent may not only be considered impractical, but also does not teach a safe locking mechanism over the needle. In fact, as the capping system is apparently contemplated, the cap is not locked in place over the needle and may in fact slide out of the needle cap, if the cap is urged towards the base of the needle, exposing it. Therefore, if one were to bump or sit atop the cap, the cap could slide back, sticking and potentially infecting that person.

Patent 6213987 issued Apr. 10, 2001 teaches a "Shroud for a Used Hypodermic Syringe Needle" wherein a longitudinally situated slide is mounted to a syringe via guide rails which in turn communicate with a front ring configured to fit a "coupling collar", a second ring configured to encompass the syringe barrel, and a rear tang which engages the syringe flange. Unlike the present invention, the '987 patent relates to a specific "locking means on said guide and said slide operable upon extension of the slide for locking the slide extended in place relative the guide".

Further, the '987 device has a front hub which engages the syringe collar and the protective shroud does not appear to actually engage the needle tip; accordingly, the needle and hub (also called cannula hub) area are not supported so that even after the device has been engaged, the needle can still come loose separate from the syringe, which can cause a needle stick. Further many of the larger sized, and European syringes do not have a collar.

Finally, patents 5,215,534 and 5,312,372 to the present applicants teach a "Safety Syringe System" which may be implemented with an "off-the-shelf plunger type syringe" ('372 Column 5, lines 15–16), as well as other needled devices, wherein there is shown mounted to the syringe a protective cover configured to "longitudinally envelope the base of the needle in a storage position, and engage and cap the needle tip in a protected configuration after the instrument has been utilized; bias means associated with said protective cover . . . ", and a "cap locking hatch" associated with said protective cover "to form a barrier juxtaposed to the needle tip and said egress aperture of said protective cover upon said needle tip being withdrawn into said protective cover". The contents of the U.S. Pat. Nos. 5,312,372 and 5,215,534 patents, filed May 13, 1994 and Dec. 2, 1991 respectively, are incorporated into the present application by reference thereto.

There is no doubt that many patents on safety syringes have issued since the '372 and '534 Deharde patents were issued; nonetheless, most safety syringes on the market are still manually operated; i.e., the operator must grasp and pull or push the protective cover or sheath in place. Such operations does not provide the desired "activate and forget" operation of the above DeHarde patents and the present application, which adopts the earlier '372 and '534 patents for operations with a variety of off-the-shelf syringe configurations.

GENERAL SUMMARY DISCUSSION OF THE INVENTION

The present invention provides a safety syringe system which is effective in use, reliable in operation, inexpensive to implement, and adaptable to a variety of needle device configurations.

Unlike the prior art, the present invention provides a simple system for adapting an off-the-shelf syringe for push button actuation of a needle cap after use which may include one-way (at the cap) as well as redundant locking means, wherein locking is provided at the cap as well as well as a locking system in the initiating mechanism (similar to that taught in the DeHarde '372 and '534 patents). This is done in an easy, push-button system designed to be literally fool proof and tamper proof.

What distinguishes the present invention from the earlier DeHarde patents is the mounting mechanism to allow the system to be mounted to a variety of off-the-shelf needle devices, which may include syringes, IV cannulas, and other devices.

The present invention also teaches an activation tab configuration for initiation of the system which is believed to be more reliable and better suited for a system configured to convert an off-the-shelf syringe to a safety syringe.

The present invention also teaches a self-actuating safety syringe wherein the plunger mechanism of the syringe engages the activation tab to deploy the protective cover, providing an automatic shielding of the needle tip once the needle has left the patient's body.

The preferred embodiment is configured to mount to an off-the-shelf syringe via threaded, snap, or permanent engagement to the mounting collar of the syringe, wherein the device may include the needle for mounting to the syringe, or in an alternative embodiment, via barrel rings configured to mount about the barrel of the syringe. This engagement at the cannula hub, coupled with the protective cover which actually engages the needle tip via the hatch when in the deployed position, actually reinforces the needle area to prevent needle breakaway after the protective cover has been deployed over the needle tip.

In the initiation mechanism, there is provided a spring biased push-button or activation tab and shaft arrangement, wherein the shaft moves longitudinally along its enveloping sleeve until it activates a one-way locking mechanism, while simultaneously biasing the protective cap along the needle until it covers the tip of the needle. Once the needle tip has been covered, the one-way locking mechanism in both the initiation mechanism and protective cover engage, preventing any subsequent needle stick or re-use.

It is therefore an object of the present invention to provide a system for preventing needle stick which incorporates protective cover locking means configured to be mounted to an off-the-shelf syringe.

It is another object of the present invention to provide a system for preventing needle stick wherein there is included a activation tab initiating system incorporating a longitudinal migrating shaft and enveloping sheath for urging a protective cap along a needle, covering it.

It is another object of the present invention to provide a system for preventing needle stick, wherein there is implemented a protective sheath or cover for the needle which permanently locks in place once it slides over the tip of the needle.

Lastly, it is an object of the present invention to provide a system for converting a variety of configuration of needle device to prevent needle stick or the like, wherein there is provided a device configured to engage said needle device via the cannula hub, providing a sheath which automatically covers the needle tip upon actuation.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein:

FIG. 1A illustrates a side view of the preferred embodiment of the safety syringe device of the present invention, illustrating the housing, cannula hub, and needle for attachment to an off-the-shelf syringe.

FIG. 1B illustrates a side view of the invention of FIG. 1A, illustrating the housing threadingly mounted to an exemplary syringe via the cannula hub, and further illustrating the protective cover at the base of the needle, longitudinal shaft, and activation tab.

FIG. 1C illustrates the invention of FIG. 1B in a deployed position, wherein the activation tab has been triggered, causing the protective cover to slide over the needle tip.

FIG. 2A is a side view of an exemplary embodiment of the invention of FIG. 1A, wherein the housing is mounted to the syringe via front and rear mounting rings.

FIG. 2B is a side view of the invention of FIG. 2A mounted to a syringe with a protective cover at the base of the needle, as well as the longitudinal shaft and activation tab.

FIG. 2C illustrates the invention of FIG. 1C in a deployed position, wherein the activation tab has been triggered, causing the protective cover to slide over the needle tip.

FIG. 9A is a side view of an alternative embodiment of the invention of FIG. 8A, illustrating the device with a cannula hub attachment as shown in FIG. 1A.

FIG. 9B is a side view of the invention of FIG. 9A illustrating the manual deployment of the protective cover by advancing the activation piece.

Detailed Discussion of the Invention

Figure 3A:
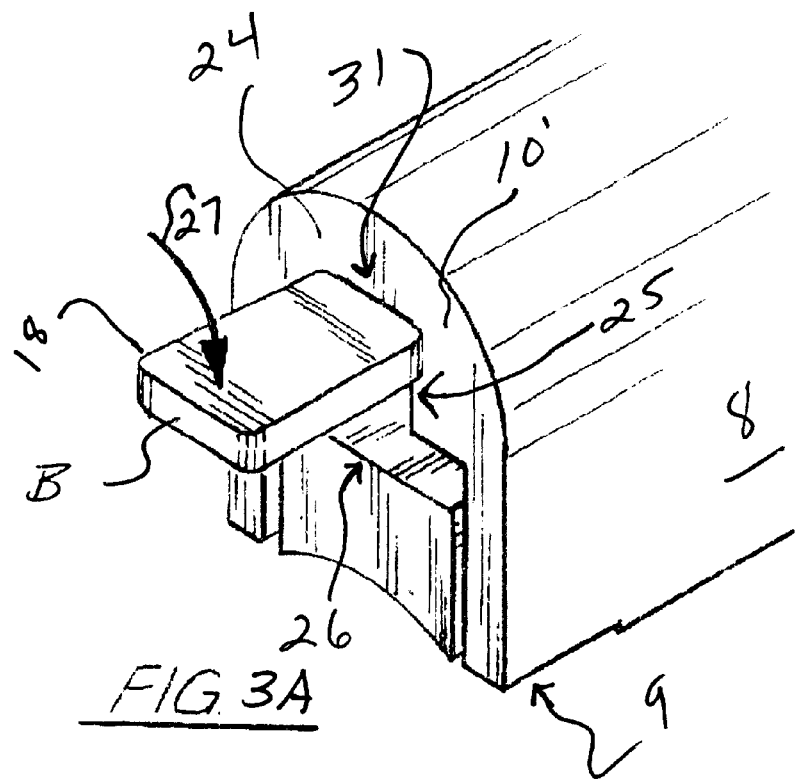
FIG. 3A is a close-up, isometric view of the activation tab of the inventions of FIGS. 1A and 2A, illustrating the tab in its un-deployed position.
Figure 3B:
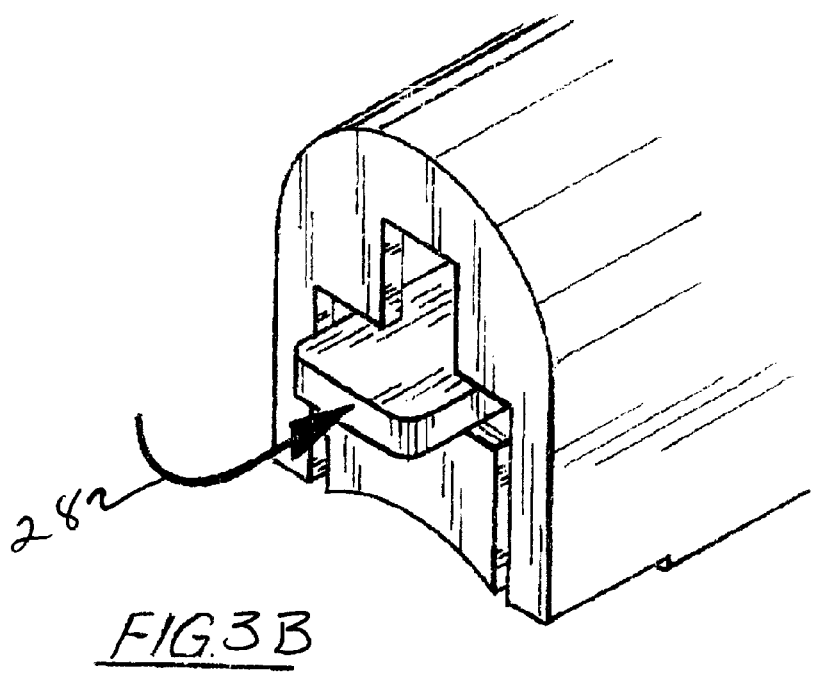
FIG. 3B is a close-up, isometric view of the activation tab of the invention of FIG. 3A, illustrating the triggering of the tab, and its movement through the slot to allow the protective cover to be urged over the needle tip.

Referring to FIGS. 1A–1C, the preferred embodiment of the present invention contemplates a device 1 configured to engage and convert a syringe 2 or other needle device so as to provide enhanced needle sheathing capability. The syringe 2 shown includes a body or barrel 3 having an outer diameter 3', a collar 4, a reservoir 5 configured to receive a plunger 6, and first 7 and second 7' ends.

The device 1 of the preferred embodiment of the present invention includes a housing 8 having a syringe engaging portion 9 configured to engage the outer sidewall of the barrel of the syringe, first 10 and second 10' ends, and a passage 11 formed longitudinally therethrough. Emanating from the first 10 end is a support member 12 configured to engage a cannula hub 13 having a needle 14. Thus, in the preferred embodiment of the invention, the housing has a cannula hub and needle engaged thereto.

Situated within the housing in the undeployed position is an actuation member 15 having first 16 and second 16' ends, the first end 16 communicating with a generally laterally situated support member, the support member communicating with a protective cover configured including a passage 20 configured to allow the passage of the needle 14 of the device, and a hatch 21 configured to engage the needle in the undeployed position and drop down to block the needle tip upon deployment. The second end 16' of the actuation member is configured to with an actuation tab 18 for activating the system. A shaft 17 is provided between the first 16 and second 16' ends, the shaft configured to be housed within the housing when in an undeployed position, within the longitudinal passage 11 formed through said housing. A spring 23 is configured to engage the shaft 17 within the housing 8 to provide bias for actuating the actuating member from an undeployed position wherein the protective cover is situated at the base of the needle, to a deployed position wherein the protective cover encloses the needle tip.

Continuing with FIGS. 1A–1C and 3A–3B, the second end 10' of housing 8 has an surface 24 forming an end wall having formed therein a retaining track 25 configured to allow the neck 31 of activation tab 18 therethrough, the retaining track having first upper, and second lower ends, one of said ends terminating into a triggering slot 26 forming a passageway sufficient to allow the activation tab 18 to pass therethrough.

In use, the activation tab 18 is situated in an engaged position with the retaining track 25, with the actuation member 15 situated as shown in FIG. 1B, with the spring 23 engaging in compressed fashion the second end of the shaft 17, with a bias longitudinally in the direction of the needle.

Figure 11:
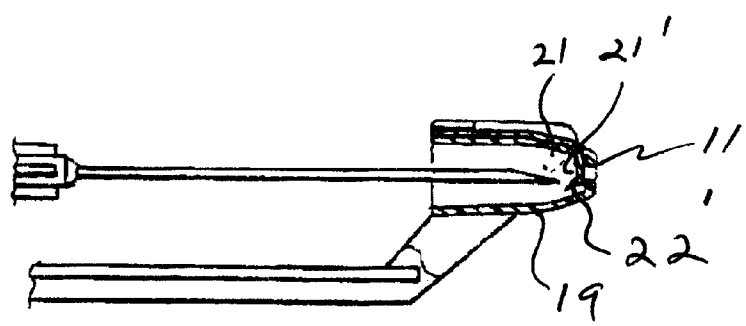
FIG. 11 is a close-up, partially cross-sectional view of the protective cover enveloping the tip of the needle, further illustrating the hatch in the deployed position.

Continuing with FIGS. 1A–1C and FIGS. 3A–3B, the activation tab 18 is pressed tab is pressed 27 or otherwise urged to glide down the retaining track 25 to the triggering slot 26, where the spring and accompanying bias urges the activation button 18 through 28 the triggering slot 26, releasing the actuation member and urging 29 via deploying spring 23' the protective cover 19 over the needle tip, the hatch 21 in the protective cap dropping 21' to block needle egress through passage 11, thereby effectively enveloping the needle tip, as shown in FIG. 11. As shown, the hatch may include a notch 22' for further locking the needle tip within the cap, such that the notch angularly intersects the needle tip when the needle tip is pressed against the hatch.

A stop 30, lock or the like may be provided in the longitudinal passage formed in the housing to facilitate the second end of the shaft remaining in the longitudinal passage formed in the housing, with the protective cover enveloping the needle tip 14' with the actuation member in the deployed position. The stop 30 may be pliant in one direction so as to allow the second end of the actuation member to be slipped thereby when inserting same though the opening at the first end of the housing during assembly.

Alternatively, the activation tab could be considered as having a body B outside of the housing, which could be broken or snapped off by the user, so as to allow the neck portion 31 to pass through the retaining track 25 and deploy the system.

Continuing with FIGS. 2A–2C and FIG. 4, as second embodiment 41 of the invention provides a device configured to convert an off-the-shelf syringe to a safety syringe wherein the housing 41 has first 42 and second 42' ends, an end wall 43, and front 44 and rear 55 rings, each ring having an inner diameter 55' sufficient to envelope the outer diameter 3 or the syringe 2.

As further shown, the rear ring 55 is configured to slip about the outer diameter of the barrel of the syringe, while the front ring 44 is configured to slip about the base of the cannula hub 48. A tang 46 is further provided to engage the flange 47 at the syringe barrel to retain the housing in locked position over the syringe once installed. The tang may have an upper edge in the form of a cam 49 or otherwise angled to allow the tang 46 to slide under then engage the side of the syringe barrel flange 47 distal the barrel. To install, the housing is slipped over the needle end of the syringe such that the rear ring 55 slides 53 over a portion of the syringe barrel, and the small ring has a diameter which stops and engages the base of the cannula hub, while simultaneously the cam formed on the end edge of the tang contacts the flange, urging the tang to pass under 54 then up 54' so as to engage the flange, locking the unit in place.

Figure 4:
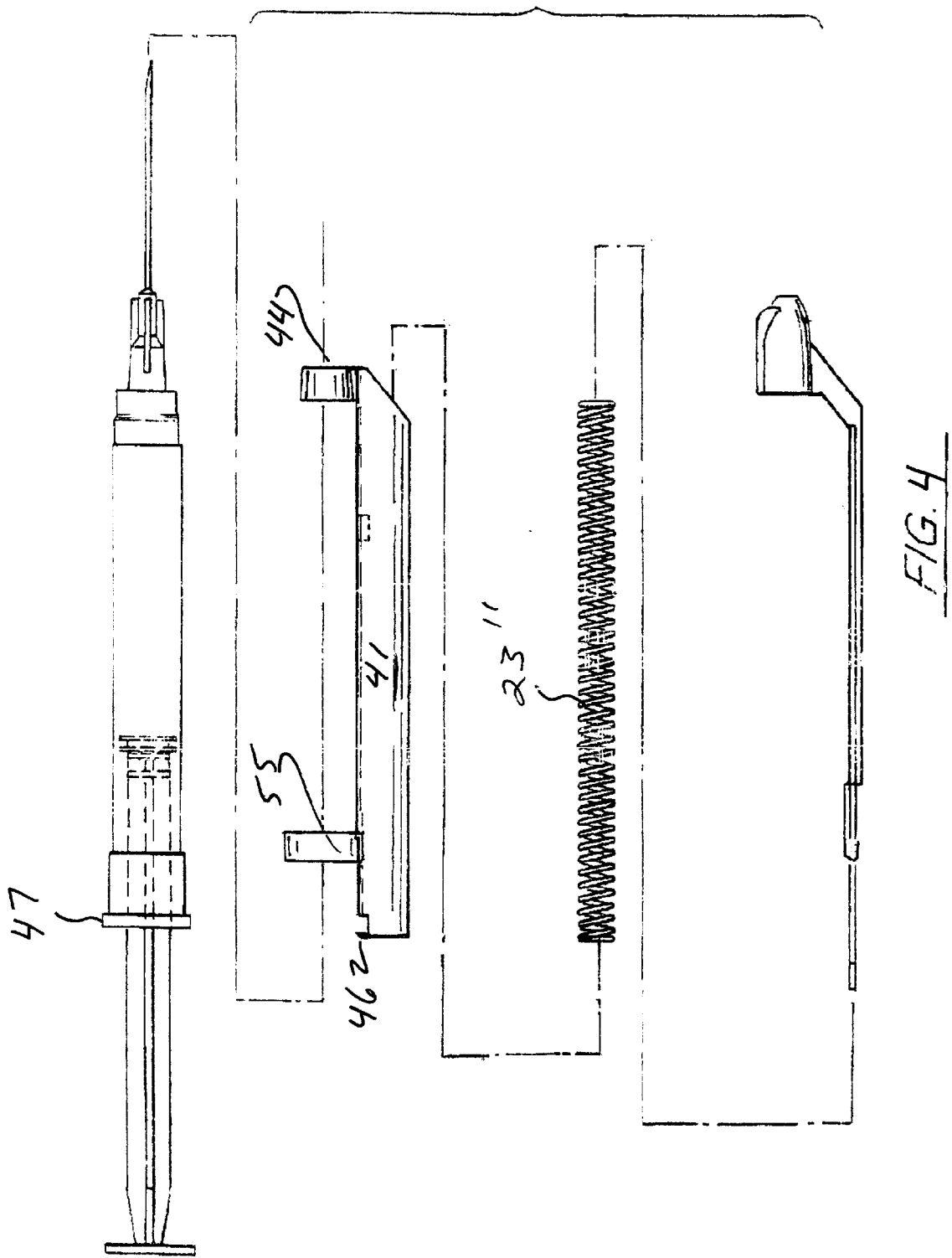
FIG. 4 is a side, exploded view of the invention of FIGS. 2A–2C, illustrating the various components forming the invention and their assembly.

The operation of the activation tab of the device, and the activation of the unit utilizing spring 23' for bias as illustrated in FIGS. 2C and 4 is otherwise identical to that discussed in the preferred embodiment of the invention supra.

Figure 5A:
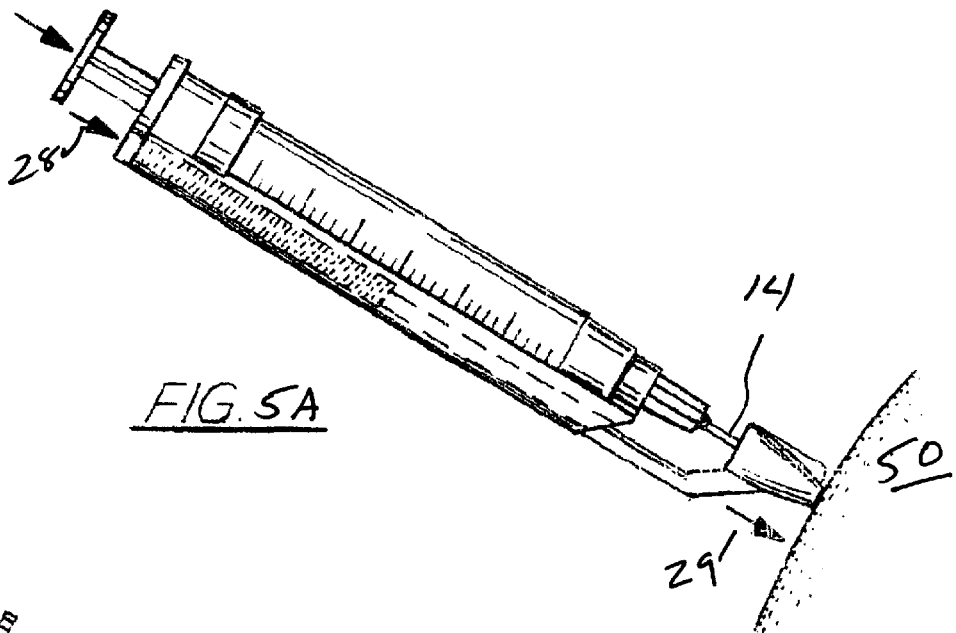
FIG. 5A is a side view of the invention of FIGS. 2A–2C, illustrating the use of a syringe in administering a shot to a patient, and the triggering of the activation tab to cause the protective cover to advance to the skin of the patient while the needle tip is still in the body of the patient.
Figure 5B:
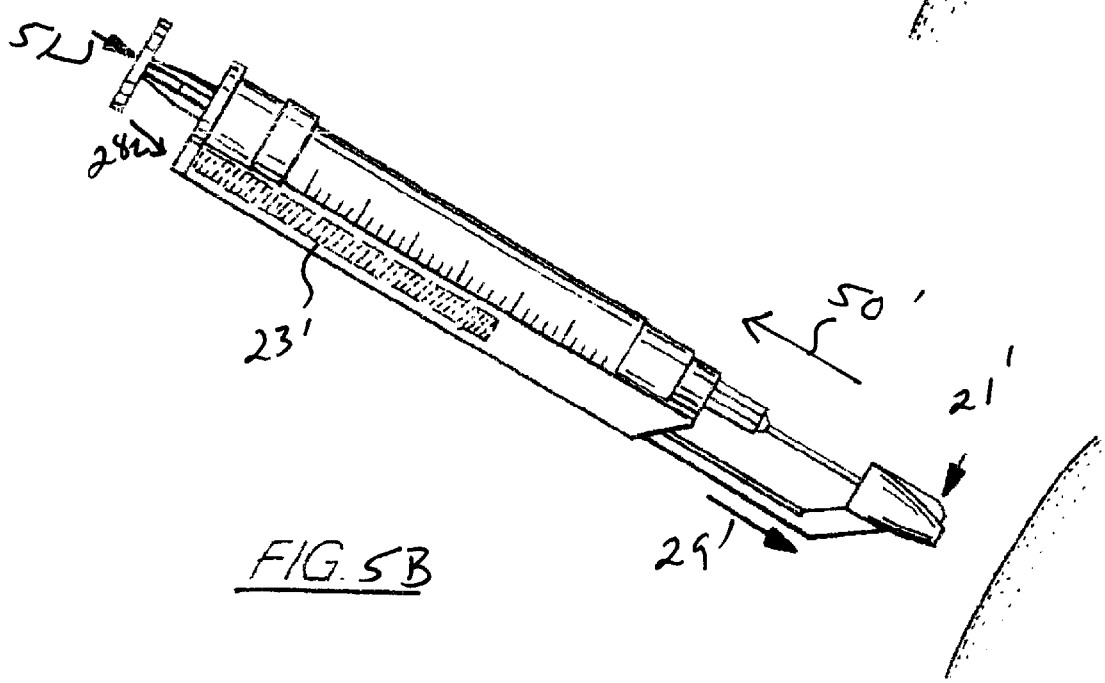
FIG. 5B is a side view of the invention of FIG. 5A, wherein the spring bias causes the protective cover to further advance to cover the needle tip as the needle is removed from the patient's skin, causing covering of the needle tip concurrent with removal of same from the patient.

FIGS. 5A and 5B illustrate a method of use of the present invention wherein 1) a syringe is provided, the housing is slipped over and joined to the syringe body; 2) the needle 14 is administered 51 in a patient's body; 4) while the needle is still in the body 50, the activation tab is initiated 28 causing same to withdraw into the housing, the spring bias 23' urging the protective cap engage the body of the patient, and 5) the syringe withdrawn 50' while allowing the spring bias to simultaneously urge the protective cap over the needle tip, so as to cover 21 same as the needle tip is removed from the patient.

Figure 6A:
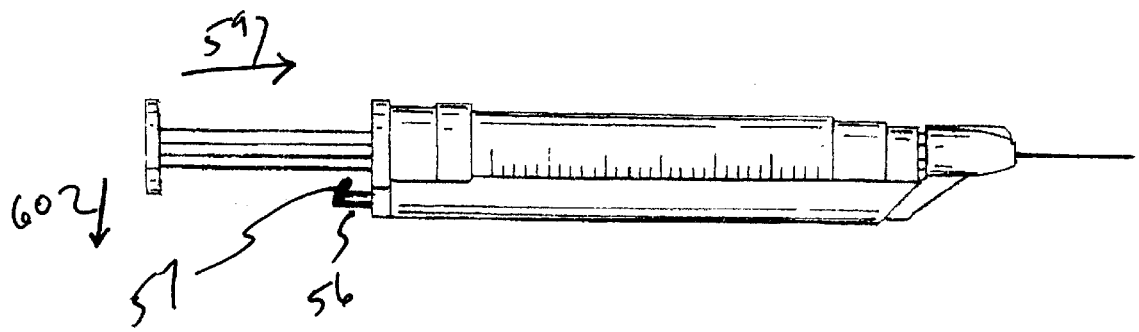
FIG. 6A is a side view of an alternative embodiment of the invention, illustrating an activation tab configured to engage the syringe plunger flange upon the administering of the syringe upon a patient.
Figure 6B:
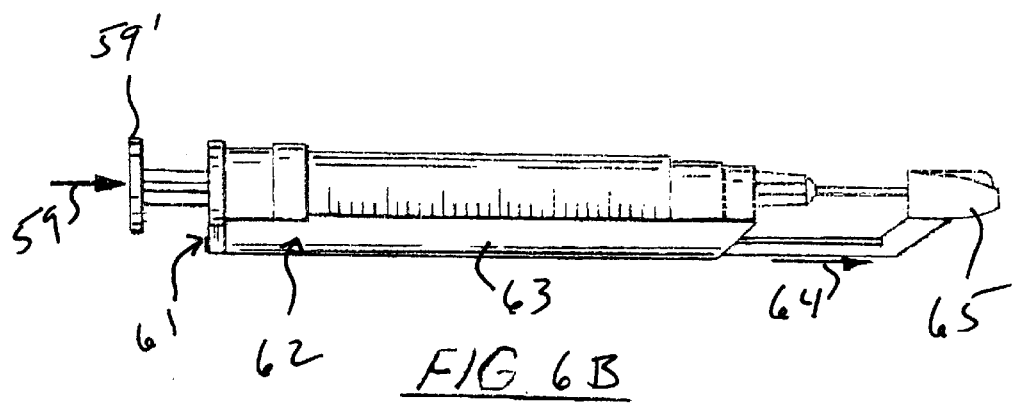
FIG. 6B is a side view of the invention of FIG. 6A, wherein the activation tab has been triggered due to contact with the plunger flange.

Continuing with FIGS. 6A and 6B, a third embodiment of the present invention extends the activation tab and provides a cam 57 or taper on the tip so as to communicate with the thumb flange on the syringe plunger upon fully depressing the plunger so that, upon the administering of a fluid to a patient via the syringe, the plunger is depressed 59 to a point where the thumb flange 59' engages the flange 57, directing 60 the activation tab 56 to the triggering slot 61 so that the spring 62 within the housing 63 is able to then urge 64 the cover 65 over the needle tip.

Figure 7:
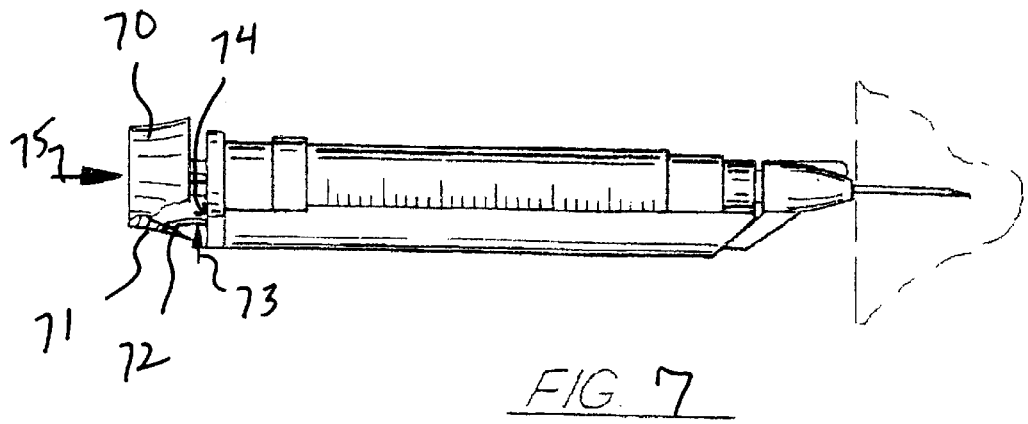
FIG. 7 is a side view of still another embodiment of the invention of FIG. 6A, wherein the plunger flange is formed to include a cam for lifting and triggering the activation tab.
Figure 8A:
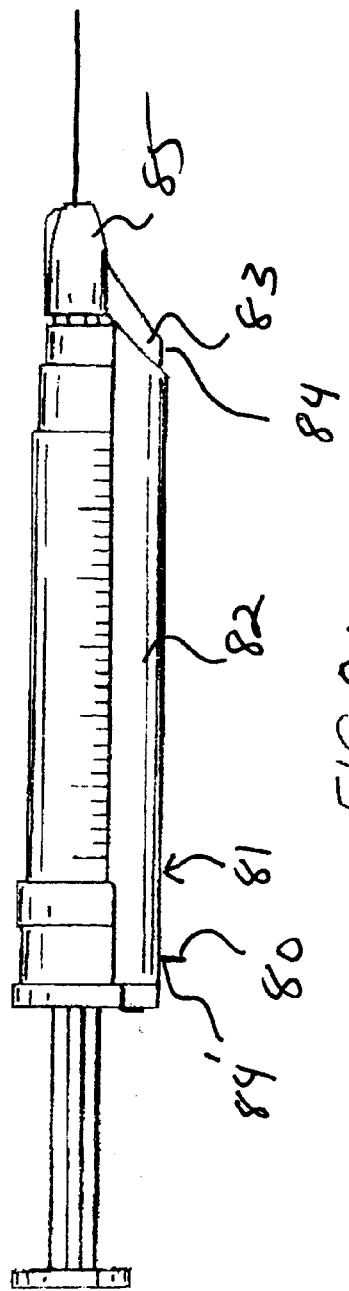
FIG. 8A is a side view of still another embodiment of the invention, wherein there is provided an activation piece which is manually urged toward the needle upon after administering the syringe.
Figure 8B:
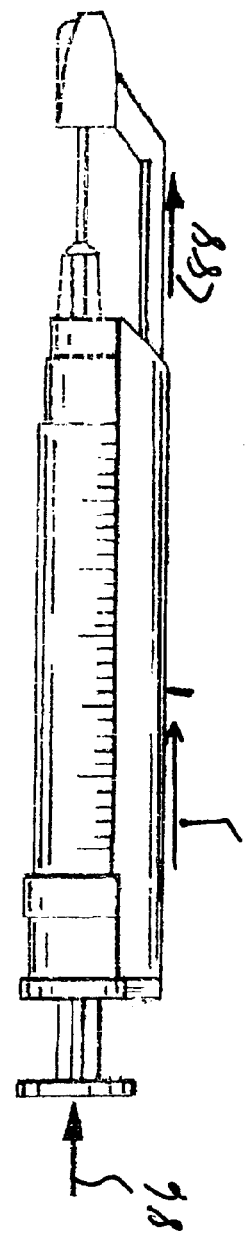
FIG. 8B is a side view of the invention of FIG. 8A illustrating the manual deployment of the protective cover by advancing the activation piece.

FIG. 7 illustrates a fourth embodiment of the present invention, where the plunger thumb flange 70 has a built-in cam 71 configured to engage the activation tab 72 to urge 73 the activation tab to the triggering slot 74 upon administering 75 the plunger.

Figure 10A:
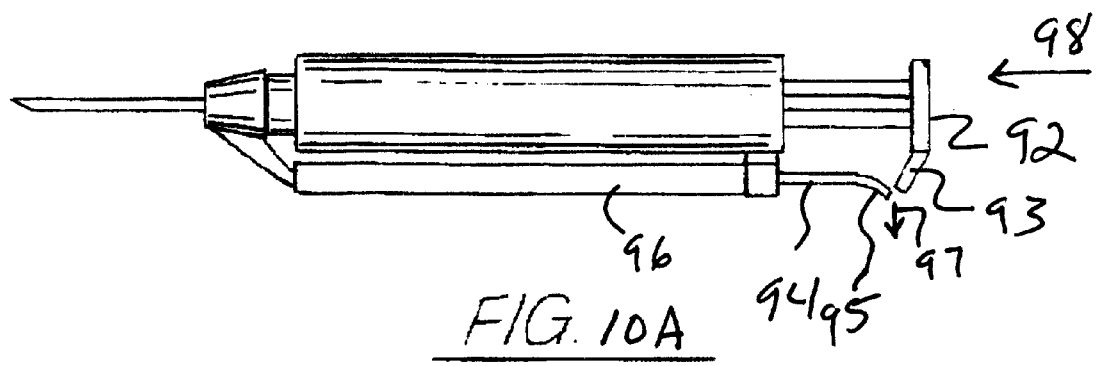
FIG. 10A is a side view of an alternative embodiment of the invention of FIG. 6A, wherein the administration of the plunger triggers the activation tab.
Figure 10B:
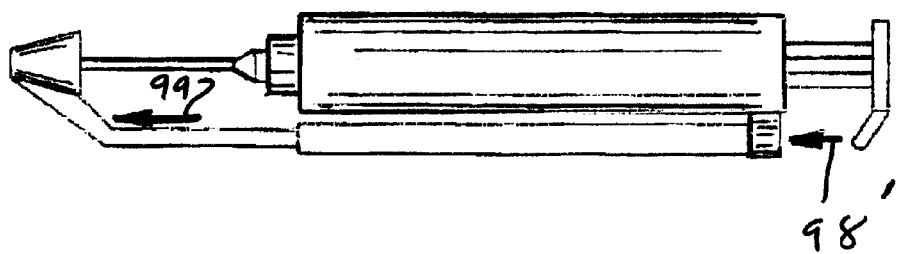
FIG. 10B is a side view of the invention of FIG. 10A, illustrating the triggering of the activation tab.

FIGS. 10A–10B illustrate another variation of the self-actuating syringe concept, wherein the plunger flange 92 has emanating therefrom a angled activation member 93, configured to engage a cam 95 emanating from the activation piece 94 to urge 97 the activation piece for triggered activation 98' with the pressing 98 of the plunger, allowing bias to urge 99 the protective cover over the needle tip.

FIGS. 8A–8B and 9A–9B illustrate a fifth alternative embodiment of the present invention, wherein the housing 82 does not utilize a spring bias to drive the activation piece 83, instead relying upon manual activation by the user wherein the housing has formed therethrough a longitudinal slot 81 along its length to accommodate the passage of an activation member 80 which in turn communicates with the shaft at the second end of the activation piece 83, so that urging 87 the activation member 80 along the slot from the generally the second end 84' of the housing toward the first end 84 of the housing urges 88 the protective cover 85 over the needle tip, which procedure is accomplished once the shot is administered 86 via the plunger.

In summary, the present invention provides a secure, reliable device for mounting to an off-the-shelf syringe for converting same to a safety syringe. The cannula hub connection to the housing, via either permanent connection or cannula hub engaging ring, coupled with the protective cover's closed enveloping of the needle tip with the hatch, also provides a reinforced needle area when the unit is deployed to prevent the needle from breaking from the cannula hub or syringe, should the deployed syringe be sat or steped upon, or otherwise jarred or stressed.

The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

Elements of the Invention
Date: Tuesday, Jul. 17, 2001 08:28 pm
Client: DeHarde
Title: Safety Syringe Sys III

| Element | Description |
| --- | --- |
| 1 | invention |
| 2 | syringe |
| 3,' | body outer diameter |
| 4 | collar |
| 5 | reservoir |
| 6 | plunger |
| 7,' | first, second ends |
| 8 | housing |
| 9 | syringe engaging portion |
| 10,' | first, second ends |
| 11 | passage therethrough |
| 12 | support member |
| 13 | cannula |
| 14 | needle |
| 15 | actuation member |
| 16,' | first second ends |
| 17 | shaft |
| 18 | actuation tab |
| 19 | protective cover |
| 20 | passage |
| 21,' | hatch, deployed |
| 22, | lateral member, hatch notch or bend |
| 23,' | spring, deployed |
| 24 | back wall |
| 25 | retaining track |
| 26 | triggering slot |
| 27 | pressure |
| 28 | sliding to triggering slot then through |
| 29 | urging longitudinal shaft, protective cover too needle tip |
| 30 | stop |
| 31 | neck |
| 32 | |
| 33 | |
| 34 | |

-continued

| Element | Description |
|---|---|
| 35 | |
| 36 | |
| 37 | |
| 38 | |
| 39 | |
| 40 | second altrnative |
| 41 | housing |
| 42 | first, second ends |
| 43 | back wall |
| 44 | front ring |
| 55,' | rear ring, inner diameter |
| 46 | tang |
| 47 | flange |
| 48 | cannula |
| 49 | cam |
| 50 | skin |
| 51 | shot administered |
| 52 | |
| 53 | slides |
| 54,' | down, up |
| 45 | |
| 56 | activation tab |
| 57 | cam |
| 58 | |
| 59' | plunger flange |
| 59 | plunger pressed |
| 60 | cam action |
| 61 | triggering slot |
| 62 | spring bias |
| 63 | housing |
| 64 | urge |
| 65 | cover |
| 66 | |
| 67 | |
| 68 | |
| 69 | |
| 70 | plunger flange |
| 71 | cam |
| 72 | activation tab |
| 73 | urge |
| 74 | triggering slot |
| 75 | plunger pressed |
| 76 | |
| 77 | |
| 78 | |
| 79 | |
| 80 | activation tab |
| 81 | slot |
| 82 | housing |
| 83 | activation piece |
| 84,' | first end, secont |
| 85 | protective cover |
| 86 | administer shot |
| 87 | urge activation member towards needle |
| 88 | urging protective cover towards needle |
| 89 | |
| 90 | |
| 91 | |
| 92 | plunger flange |
| 93 | cam |
| 94 | activation piece |
| 95 | cam |
| 96 | housing |
| 97 | urge |
| 98 | plunger pressed |
| 98' | triggering activation |
| 99 | urging cover over needle tip |
| 100 | |

What is claimed is:

1. A device for preventing needle stick when utilizing a fluid administering device having a barrel having first and second ends and a length, the barrel forming a fluid reservoir having first and second ends, the first end of the barrel having a collar, comprising:

a housing having first and second ends and a length, said first end having a cannula hub affixed thereto, said cannula hub having a needle emanating therefrom, said needle having a needle tip, said cannula hub configured to engage said fluid administering device, said cannula hub formed to engage the collar of said fluid administering device such that said housing is secured adjacent to the barrel along the barrel's length, such that said second end of said housing is adjacent to said second end of the barrel, and said first end of said housing is adjacent to said first end of the barrel;

an activation member having a shaft having first and second ends, said first end having a protective cap having a needle passage therethrough, said activation member configured to slidingly engage said housing;

bias means associated with said activation member for urging said activation member;

an activation tab associated with said second end of said activation member, said activation tab emanating from said second end of said housing such that when said housing is mounted to the barrel, said housing emanates past said second end of said barrel, said activation member for retaining said bias means in an undeployed position, and for releasing upon demand said bias means to a deployed position wherein said activation member urges said protective cap from a first position in the vicinity of said cannula hub to a second position enveloping said tip of said needle;

wherein said activation tab further comprises a breakaway tab configured to emanate from said second end of said housing, said breakaway tab configured so as break from said activation member when bent, allowing said bias means to urge said activation member from an undeployed position to a deployed position.

2. The device of claim 1, wherein said bias means comprises a spring in communication with said housing and said shaft of said activation member.

3. The device of claim 2, wherein said activation tab is formed to engage a triggering slot so as to release said activation member, whereupon said bias means then urges said protective cap to said second position.

4. The device of claim 3, wherein said fluid administering device is a syringe.

5. Method of administering a needled device, comprising the steps of:

a. providing a device for preventing needle stick when utilizing a medical apparatus having a barrel having first and second ends and a length, the barrel forming a fluid reservoir having first and second ends, the first end of the barrel having a collar, said device comprising:

i. a housing having first and second ends, said first end having a cannula hub affixed thereto, said cannula hub having a needle emanating therefrom, said needle having a needle tip; said cannula hub configured to engage said medical apparatus, said cannula hub formed to engage the collar of said medical apparatus such that said housing is secured adjacent to the barrel along the barrel's length, such that said second end of said housing is adjacent to said second end of the barrel, and said first end of said housing is adjacent to said first end of the barrel;

ii. an activation member having a shaft having first and second ends, said first end having a protective cap having a needle passage therethrough, said activation member configured to slidingly engage said housing;

iii. bias means associated with said activation member for urging said activation member; and an activation tab associated with said second end of said activation member, said activation tab emanating from said second end of said housing such that when said housing is mounted to the barrel, said housing emanates past said second end of said barrel, said activation tab for retaining said bias means in an undeployed position, and for releasing upon demand said bias means to a deployed position wherein said activation member urges said protective cap from a first position in the vicinity of said cannula hub to a second position enveloping said tip of said needle, said activation tab further comprising a breakaway tab configured to emanate from said second end of said housing, said breakaway tab configured so as break from said activation member when bent, allowing said bias means to urge said activation member from an undeployed position to a deployed position;

b. mounting said cannula hub of said device to said collar of said medical apparatus;

c. allowing said mounting of said cannula hub to said collar of said medical apparatus to facilitate positioning of said housing along the length of said barrel of said medical apparatus;

d. administering said medical apparatus at said second end of said medical apparatus;

e. initiating said activation tab to slidingly traverse said housing so as to urge said protective cap from said first position in the vicinity of said cannula hub to said second position wherein said protective cap envelopes said needle tip, by bending said breakaway tab, breaking same from said activation tab, and allowing said bias means to urge said activation member from an undeployed position to a deployed position.

6. The method of claim 5, wherein there is provided the additional step in step "d" of inserting said needle into a patient, and in step "e" there is provided the additional step of bending said breakaway tab, breaking same from said activation piece, and allowing said bias means to urge said activation member from an undeployed position to a deployed position while said needle is still in said patient, and there is provided the additional step "e" of withdrawing said needle from said patient while simultaneously allowing said bias means to slide over said needle as said needle is being removed from said skin, so as to envelope the tip of said needle upon removal from the patient.

* * * * *